United States Patent [19]

Dietz

[11] Patent Number: 5,038,771
[45] Date of Patent: Aug. 13, 1991

[54] METHOD AND APPARATUS FOR RESPIRATORY THERAPY USING INTERMITTENT FLOW HAVING AUTOMATIC ADJUSTMENT OF A DOSE OF THERAPEUTIC GAS TO THE RATE OF BREATHING

[76] Inventor: Henry G. Dietz, 80 Salisbury Ave., Garden City, N.Y. 11530

[21] Appl. No.: 469,929

[22] Filed: Jan. 25, 1990

[51] Int. Cl.$^5$ ............................................ A61M 16/00
[52] U.S. Cl. ............................. 128/204.21; 128/204.33
[58] Field of Search ...................... 128/204.18, 204.21, 128/204.23

[56] References Cited

U.S. PATENT DOCUMENTS

| | | | |
|---|---|---|---|
| 3,961,627 | 6/1976 | Ernst et al. ...................... | 128/204.21 |
| 4,001,700 | 1/1977 | Cook et al. ...................... | 128/204.21 |
| 4,036,221 | 7/1977 | Hillsman et al. ................ | 128/204.23 |
| 4,256,100 | 3/1981 | Levy et al. ...................... | 128/204.21 |
| 4,323,064 | 4/1982 | Hoenig et al. .................. | 128/204.21 |
| 4,380,233 | 4/1983 | Caillot ............................. | 128/204.21 |
| 4,393,869 | 7/1983 | Boyarsky et al. ............... | 128/204.21 |
| 4,401,115 | 8/1983 | Monnier .......................... | 128/204.23 |
| 4,665,911 | 5/1987 | Williams et al. ................ | 128/204.21 |

Primary Examiner—Edgar S. Burr
Assistant Examiner—Aaron J. Lewis

[57] ABSTRACT

A method and apparatus for sensing when inspiration takes place during breathing cycles of air-breathing animals, including humans, that triggers a dose of respiratory gas to be inhaled when inhalation begins. The dose of the respiratory gas determined by the length of the previous breath, whereby it follows from the foregoing that the dose of respiratory gas is automatically adjusted to the rate of breathing of the air-breathing animals, including humans.

4 Claims, 5 Drawing Sheets

[5,038,771]

METHOD AND APPARATUS FOR RESPIRATORY THERAPY USING INTERMITTENT FLOW HAVING AUTOMATIC ADJUSTMENT OF A DOSE OF THERAPEUTIC GAS TO THE RATE OF BREATHING

BACKGROUND OF THE INVENTION

This invention pertains to sensing when inspiration takes place during breathing cycles of air-breathing animals, including humans, that triggers a dose of therapeutic gas to be inhaled when inhalation begins, with the dose of therapeutic gas determined by the length of the previous breath, which results in automatic adjustment of the therapeutic dose to the rate of breathing of the air-breathing animal, including humans.

In this invention the sensing of inhalation and delivery of the therapeutic gas is accomplished by making a single connection between the respiratory apparatus and the air-breathing animal, including humans. This single connection can be a nasal cannula (of the type normally used for delivering oxygen therapy) or a similar device that must be relied upon both for sensing the length of breath and for delivering the triggered dose of therapeutic gas. This dual function cannot be carried on simultaneously for the dose must be terminated before the end of the breathing cycle and the length of the dose of gas must be determined from the previous breath for it is impossible to establish what the length of the next breath will be until it occurs.

A problem occurs when the previous breath is extremely long, which happens when the "sigh mechanism" takes place, which is an unusually large breath that takes place periodically.

When this occurs, the next dose, that is determined by the last breath, would be so large that the nasal cannula would not be able to sense when the next short breath takes place, because the nasal cannula would be giving a dose of therapeutic gas that is longer than the next breath.

To overcome this problem, the maximum dose of therapeutic gas is limited to 2 seconds. Thus, the maximum dose is used to trigger the next dose after a "sigh breath" occurs. Since, in this invention, the maximum adjustable dose is 50% of the previous dose, the new dose after a "sigh breath" would be a maximum of one second.

The maximum rate of breathing that can be detected after a "sigh breath" is 60 breaths per minute. Since the most rapid rate of breathing is by infants, approximately 40 breaths per minute maximum, the limiting of the dose to 2 seconds overcomes the problem created by the "sigh breaths" that periodically occur. The rate of breathing for an adult is 15 to 20 breaths per minute, and for babies 20 to 40 breaths per minute; all less than the 60 breaths per minute limitation of this invention.

In this invention the length of the dose can be adjusted as a percentage of the last breath.

In prior art, the dose is either set as a fixed length of time that is manually set, or by detecting when inhalation takes place, and terminating the dose when exhalation takes place.

If a single nasal cannula is used, it is impossible for a sensor to have the dual function of sensing and delivering the dose, as only one function at a time can take place.

The prior art taught in Greenwood, Pat. No. 4,744,356 (May 17, 1988) illustrates the requirement for a separate sensor to detect the inhalation and a nasal cannula to deliver the therapeutic gas. It lacks the feature of selecting the length of the dose as a percentage of the length of breath, for it is impossible for the Greenwood device to determine what the length of the next breath will be before it takes place.

The J.E. Finan Pat. No. 3,400,713 (Sept. 10, 1968) is similiar in operation to Greenwood, the only difference being that one employs electronic detection and the other mechanical detection.

The prior art taught in the Durkan Pat. No. 4,414,982 (Nov. 15, 1983) illustrates the use of a fixed adjustable time to manually regulate the length of the dose and requires a dual nasal cannula where one nostril is used for sensing, and the other nostril for delivering the therapeutic gas. The Durkan invention does not have the feature of automatic adjustment of the therapeutic dose to the rate of breathing and must be manually adjusted.

The invention described in this specification teaches a method for automatic adjustment of the therapeutic dose to the rate of breathing, the apparatus required, and the special combination of components necessary to accomplish this automatic adjustment.

SUMMARY OF THE INVENTION

The apparatus consists of an optoelectronic sensor (that can detect negative pressure of 0.001 of an ounce per square inch) which is connected to a user by a single connection that can be a nasal cannula or a similar device. This single connection is also used for delivering the dose of therapeutic gas after inhalation is sensed, by having a normally open valve be de-energized for the length of time of the dose that is supplied from a source of supply of therapeutic gas.

The optoelectronic sensor can be manually calibrated for proper operation by actuating a calibration switch and adjusting a calibrating potentiometer to obtain proper illumination of a light emitting diode to determine when proper adjustment is accomplished. The proper flow of therapeutic gas is adjusted at the supply source when the apparatus is not powered up and the normally open valve allows a continuous flow of therapeutic gas.

After the adjustment of the flow is made, the apparatus is powered up and the flow of therapeutic gas will not flow until the optoelectronic sensor is actuated by sensing inhalation.

The optoelectronic sensor is compensated for normal temperature variations and shock normally encountered in the type of environment where inhalation therapy apparatus is used.

The apparatus can operate from a 120 volt AC wall outlet by use of a wall transformer, or directly from any 6 to 24 volt DC source.

When the optoelectronic sensor detects inhalation after the apparatus has been powered up, a dose of the therapeutic gas will flow for whatever percentage the dose control is set for (10%, 20%, 30%, 40%, or 50%) of the previous breath. However, when the apparatus is put into operation for the first time, there is no previous breath and the operation of the apparatus is dependent on the fact that the maximum dose is limited to 2 seconds.

This limited 2 second dose then acts as the first previous dose, and as the length of breath, and makes possible a maximum dose of 1 second if the dose control is set for a maximum of 50%. Therefore, this guarantees that the dose must be less than the shortest length of breath, which would occur when a baby is breathing at a high rate of 40 breaths per minute.

This feature makes it possible to use a single connection for sensing and delivering the therapeutic gas, for the dose time will always be less than the shortest possible breath time.

The apparatus will not allow flow of the therapeutic gas unless actual inhalation is taking place.

The length of time of the dose is always some percentage (10%, 20%, 30%, 40%, or 50%) of the previous breath.

When a "sigh breath" takes place, the length of breath will make the length of the dose so large that the connection would not be able to sense the inhalation, for the connection can not simultaneously sense inhalation while supplying the therapeutic gas.

This problem is overcome by limiting the maximum dose to 2 seconds, which results in the time of the dose always being of a shorter duration than the time of the shortest breath.

The apparatus is provided with a switch to select one of two modes of operation. The first mode is as explained previously; the second mode is where the time length of the dose is made to be a fixed time selected by a manual control (0.25 to 2 seconds) and is independent of the rate of breathing.

The advantage of this apparatus over the previous art is that the length of time the dose of therapeutic gas is supplied can be some selected percentage of the last previous breath, thus providing automatic adjustment of the dose of therapeutic gas to the rate of breathing. The rate of breathing varies according to the activities of the air-breathing animals, including humans, where the lowest rate is at rest and the fastest when subject to the stress of strenuous exercise.

The built-in time limit to the length of time of the dose overcomes the problem of the "sigh mechanism" that takes place periodically and is a unique feature that is not taught in any of the prior art.

The use of this apparatus for respiratory therapy results in an intermittent flow of the therapeutic gas that results in great savings when compared to the continuous flow systems now in use.

This apparatus, for respiratory therapy, can be used from any source of supply of respiratory gas such as from an oxygen concentrator, from tanks, or from a wall outlet in a hospital.

Beside the obvious saving in the cost of respiratory gases, there are many medical advantages. The apparatus provides indication as to whether or not the patient is receiving the benefits of the therapy for it indicates if he is inhaling it. High flow of therapeutic gas at the beginning of inhalation assures most effective use of the therapeutic gas in reaching the alveolar and prevents waste of gases in the dead space of the lungs.

BRIEF DESCRIPTION OF THE DRAWINGS

The foregoing, and other objects, features, and advantages of the invention will be apparent from the following more particular description of preferred embodiments, as illustrated in the accompanying drawings in which reference characters refer to the same parts throughout the various views. The drawings are not necessarily to scale, emphasis instead being placed upon illustrating the principles of the invention.

DESCRIPTION OF THE PREFERRED EMBODIMENTS

Figure 1:
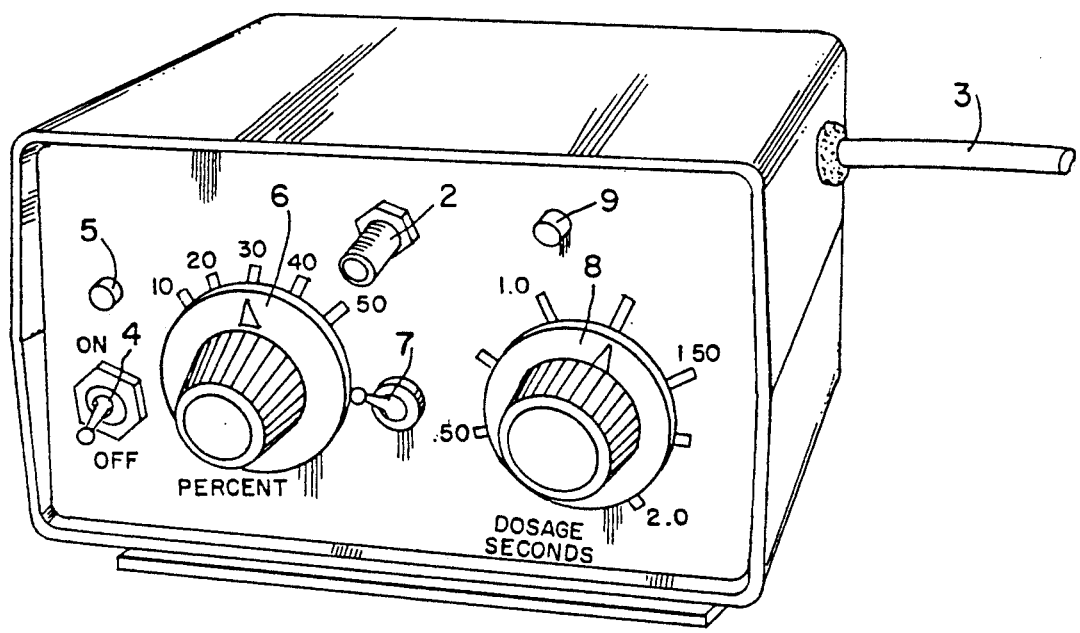
FIG. 1 is a diagrammatic front view of the respiratory therapy apparatus having automatic adjustment of the dose of therapeutic gas to the rate of breathing according to the invention.
Figure 2:
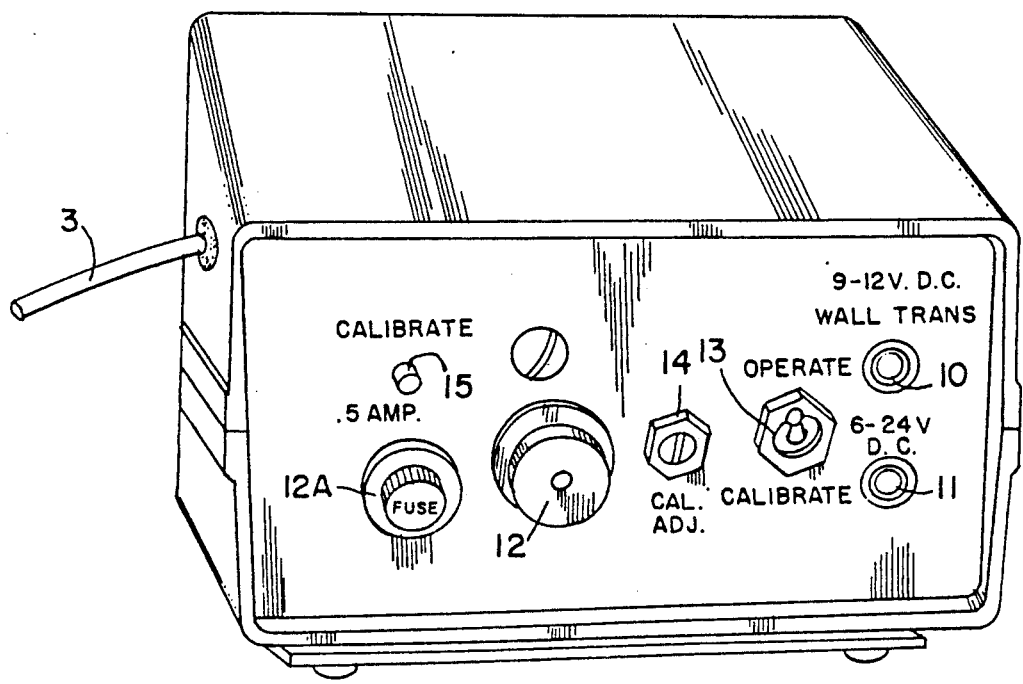
FIG. 2 is a diagrammatic rear view of the respiratory therapy apparatus having automatic adjustment of the dose of therapeutic gas to the rate of breathing according to the invention.

FIG. 1 and 2 generally illustrate the preferred embodiments of the apparatus used for respiratory therapy having automatic adjustment of the dose of therapeutic gas to the rate of breathing.

Figure 8:
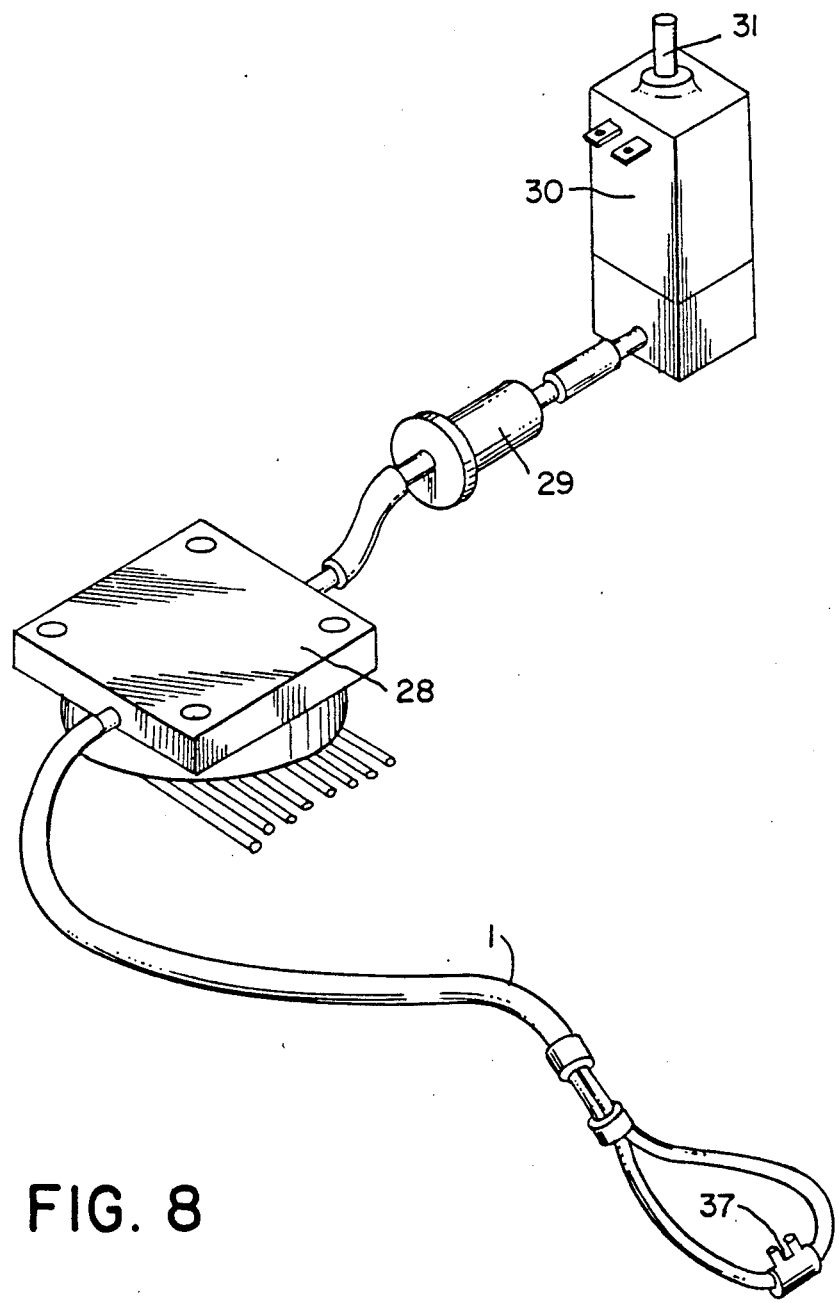
FIG. 8 is a diagrammatic view using the optoelectronic inhalation sensor for inhalation therapy in isometric projection used in the invention.

The air-breathing animal, including humans, is connected to a nasal cannula 1, FIG. 8, or similar device, and the other end of the cannula to an outlet connection 2, FIG. 1 of the respiratory therapy apparatus.

The nasal cannula 1, is used for the dual purpose of sensing inhalation by detecting the negative pressure at the nostril of the air-breathing animal, including humans; and for delivering a dose of therapeutic gas that is triggered when inhalation is sensed, and which is automatically adjusted to the correct dose in accordance with the rate of breathing.

The respiratory therapy apparatus is connected by a tube 3, FIG. 1, to an adjusted regulated flow of respiratory gas (such as 2 liters per minute) from a tank, oxygen concentrator, or a wall outlet in a hospital.

Before powering up the respiratory therapy apparatus, it is necessary that the flow of therapeutic gas be adjusted to the correct flow rate at the source of supply. The therapeutic gas will then flow through the apparatus as a continuous flow directly from tube 3, to the outlet connector 2, and to the nasal cannula 1, that supplies the therapeutic gas to the air-breathing animals, including humans.

Powering up the respiratory therapy apparatus by pressing switch 4 to the "On" position will turn the apparatus on, which will be verified by the LED 5 (light emitting diode). Immediately the flow of therapeutic gas from connection 3 will be stopped by the respiratory apparatus and no therapeutic gas will flow from the outlet connection 2.

To obtain a flow of therapeutic gas from outlet connection 2, a negative pressure must be detected from the nostrils of the air-breathing animal, including humans, wearing the nasal cannula 1.

When inhalation is first detected, a dose of therapeutic gas will be triggered. This dose can not be determined from a previous breath, but is determined by the portion of the internal circuit in the respiratory apparatus that limits any dose of therapeutic gas to two seconds.

The first dosage of therapeutic gas is based on a percentage of the time between breaths, which is controlled by turning the switch 6 to the desired percentage. The percentages available are: 10%, 20%, 30%, 40% and 50%.

The first dose will be the set percentage, such as 10% of 2 seconds, or a dose of 0.2 seconds. Thereafter, the dose will automatically be the set percentage, such as 10% of the time between breaths, unless there is an unusually large breath, such as a "sigh breath" that takes place periodically. When the "sigh mechanism" takes place, the time duration of the next dose could be larger than the length of the next breath.

If this occurs, the cannula will be delivering the therapeutic gas, and will not be able to sense inhalation to trigger the next breath.

To overcome this problem, the length of time of the dose is limited to a maximum of 2 seconds and the last breath becomes this value when a "sigh breath" (that can be over 2 seconds), takes place.

If the switch 6, is set to the maximum percentage of 50%, therefore, the next dose after a "sigh breath" would be 1 second.

The most rapid normal breathing is that of an infant; approximately 40 breaths per minute. The 1 second dose after a "sigh breath" would allow the apparatus to be usable at 60 breaths per minute, which is greater than the maximum 40 breaths required to overcome the problem.

The time of the "sigh breath" dose could be greater than the time of the next breath without the 2 second limitation, which would make the apparatus unusable without the dose limitation, for the cannula can not be used simultaneously to sense inhalation and deliver the therapeutic gas.

Switch 7, when pressed to the left, is for the first mode of operation that has been described. When switch 7, is pressed to the right, the second mode of operation is entered. In this second mode a dosage of the therapeutic gas is given to the user based on a timed dosage. The length of this timed dosage is set by the user by turning the control 8, to the desired time, such as 0.5 to 2.0 seconds.

The LED (light emitting diode) 9, lights when therapeutic gas flows, whether the unit is in mode 1 (percentage dosage) or in mode 2 (timed dosage).

The apparatus can be operated from a 120 volt AC wall outlet by use of a wall transformer that has a 9–12 volts DC output, that is provided with a plug connection that is plugged into the jack 10.

The apparatus can also be operated from a 6–24 volts DC supply, such as obtained from a car battery by using jack 11. A fuse 12A, protects the apparatus from accidental short circuits.

An overload pressure relief valve 12, protects the sensor if an accidental overload pressure is applied to tube 3.

To calibrate the apparatus for maximum sensitivity, switch 13, is pressed from the operate position to the calibrate position. Then the calibration adjustment control 14, is adjusted to just light the LED (light emitting diode) 15. When this point is reached where the LED 15 lights, control 14 is backed off to the point where LED 15 goes out. When this is accomplished, the apparatus is calibrated and switch 13 pressed to the operate position.

The apparatus is then ready for use.

Figure 3:
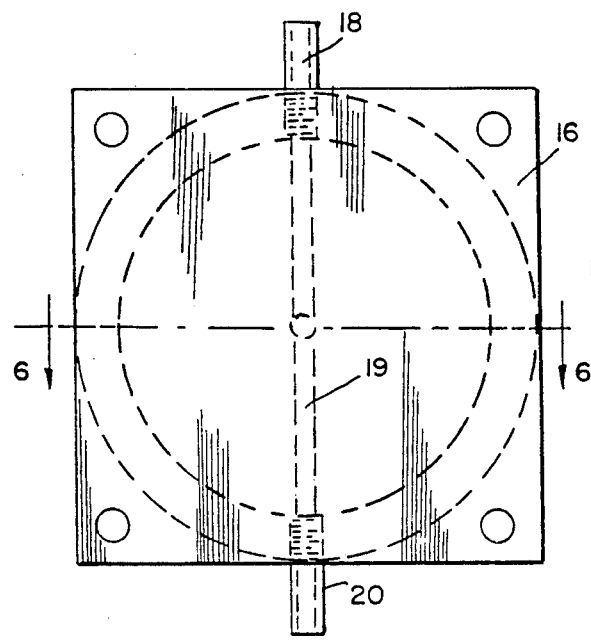
FIG. 3 is a top view of the optoelectronic inhalation sensor used in the invention.
Figure 4:
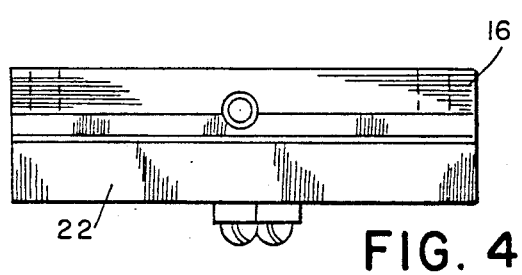
FIG. 4 is a front elevation view of the optoelectronic inhalation sensor used in the invention.
Figure 6:
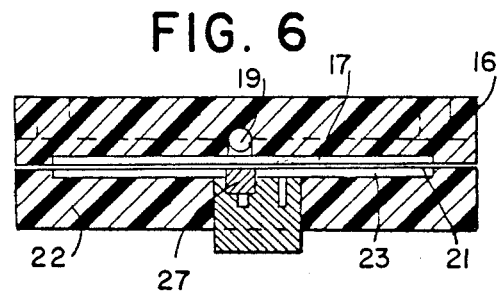
FIG. 6 is a section taken along section 6—6 of FIG. 3.
Figure 5:
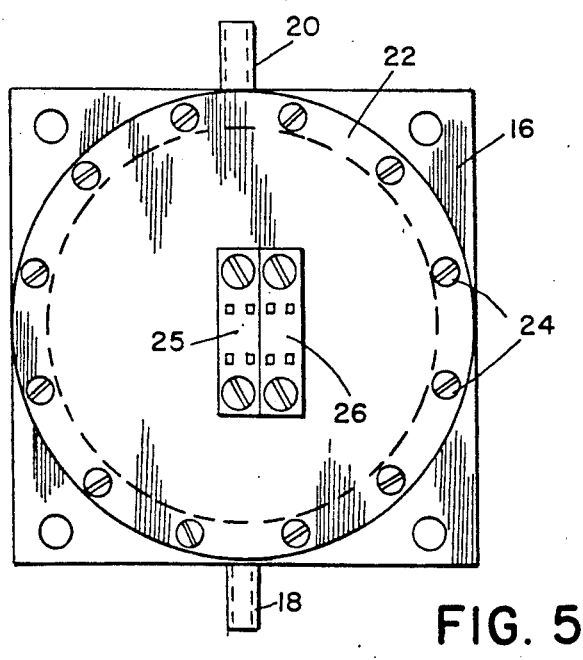
FIG. 5 is a bottom view of the optoelectronic inhalation sensor used in the invention.
Figure 7:
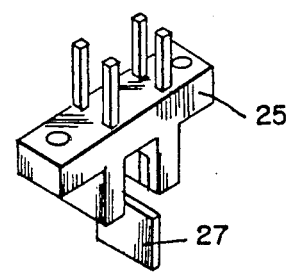
FIG. 7 is a diagrammatic view of the optoelectronic solid state photo coupled interrupter module used in the optoelectronic inhalation sensor in isometric projection.

FIG. 3, 4, and 5 generally illustrate a preferred embodiment of an optoelectronic inhalation sensor, which comprises a square housing 16, made of a rectangular opaque material in cross section FIG. 6, having a circular recess forming a central cavity 17, therein, the square housing 16, having an inlet connection 18 through one end thereof, with a passageway 19, and another outlet connection 20, through the other end of the square housing; both inlet and outlet passages being in direct communication with the central cavity 17, in the square housing 16.

The flow of therapeutic gas into the inlet connection 18, passageway 19, with outlet connection 20, creates a suction in central cavity 17. This slight suction is used as an eductor to clear out any moisture that may have been entrapped in central cavity 17, which, if not removed, could affect operation of the sensor.

The diaphragm 21, is a 0.0005 inch thick polyester film or other equally suitable thin flexible material. The diaphragm 21 is pre-stressed circumferentially and bonded to the surface of the square housing 52, forming a space between the recessed central cavity 17, of housing 16, and the film diaphragm 21. This space changes when a patient inhales, becoming smaller when inhalation takes place.

A clamping disc 22, made of opaque material in cross section FIG. 6, having a circular recess forming a central cavity 23, is fastened to the square housing 16, by a plurality of screws 24.

The circular recess forming the lower central cavity 23 is vented to the outside atmospheric pressure. The depth of the circular recess forming the central cavity 23 is minimum, such as 0.005 inch deep, being used to limit the movement of the film diaphragm 21, to prevent the film diaphragm 21 from being stretched when therapeutic gases with high pressure of 10 pounds per square inch, are supplied to the upper central cavity 17. For best operation of the optoelectronic inhalation sensor, the clamping disc 22 should be located at the bottom of the sensor. With changes in temperature, the diaphragm 21 can expand or contract, however, due to the limited depth of the recess, and due to the force of gravity, the diaphragm will always be in close proximity to the set calibration point, which is the point where the film diaphragm 21 is flat with no pressure on either side.

In the center of the clamping disc 22 is a rectangular opening to accept two optoelectronic solid state photon coupled interrupter modules 25 and 26. Module 25 is located in the center of disc 22, and provides an electrical output when the infrared-opaque vane 27 is moved upward by the film diaphragm 21. Module 26 is located as near as possible to module 25. Module 26 is used as an inactive unit to provide a reference for temperature compensation.

The electrical output of the optoelectronic solid state photon coupled interrupter module 25 occurs when a negative inhalation pressure is applied to the upper central cavity 17, moving the vane 27 upward to allow passage of the infrared light.

The diaphragm 21 will be actuated by a small volume of negative inhalation pressure of 0.001 ounce per square inch, which will move the infrared-opaque vane 27 up to signal switching the output from an "Off" state to an "On" state.

The "On" state will trigger a prescribed dose of therapeutic gas at high pressure forcing the diaphragm 21 into the lower cavity 23, and preparing it for the next inhalation, when the diaphragm 21 will be sucked up into the central cavity 17.

FIG. 8 shows a method for using an optoelectronic inhalation sensor for respiratory therapy. A cannula 1, commonly available in hospitals for administering oxygen, is used to connect the flow of air from a user's nostrils to the optoelectronic inhalation sensor 28 described, by using the outlet connection 20, FIG. 3.

The filter 29 can be placed as shown on FIG. 8, or inserted between the cannula 1 and optoelectronic inhalation sensor 28. Its purpose is to prevent any foreign object, that might be present in the gas supply, being inhaled into the user's lungs.

The optoelectronic inhalation sensor is connected to the normally open solenoid valve 30 by means of appropriate tubing using the inlet connection 18 of the inhalation sensor 28. The solenoid valve 30 is electrically activated by low voltage and low current, that can be supplied by an electronic circuit that can be designed to be intrinsically safe (a circuit that is incapable of having a spark or thermal effect that would be capable of causing ignition of flammable or combustible material in the gas being used for respiratory therapy). The connection 31 on the solenoid valve 30 is connected to the supply of gas being used for therapy.

Cannula 1 is adjusted to fit the user so that the two prongs 37 are inserted into the user's nostrils. The inhalation flow of air from the user's nostrils produces a very low pressure or vacuum at the end connected to the inhalation sensor 28.

The vacuum pressure produced by the user inhaling is no more than a few thousandths of an ounce per square inch. At the time the user is exhaling, the electric solenoid valve 30 is electrically activated and shuts off the flow of gas from the therapeutic gas supply being used. When the user inhales, the thin film diaphragm 21 is sucked up into the upper central cavity 17, moving the infrared-opaque vane 27 upward to cause an electrical signal to an "On" state. With appropriate electrical circuits as described in this patent specification: in 1st mode of operation, a signal is sent to cause a flow of therapeutic gas that delivers a dose automatically adjusted to the rate of breathing; in the 2nd mode of operation a signal is sent for a pre-determined time. These electrical signals cause the flow of therapeutic gas by electrically deactuating the normally open valve 30. In actual practice, it has been found that the flow of air being sucked in by the user is at a maximum for a very short period of time, and this peak flow of air vacuum from the user's nostrils is used to trigger the flow of the therapeutic gas.

Mode of operation 1 and 2, provides for an intermittent flow of therapeutic gas to the user. The user normally inhales for approximately 30% of the time for each breath, with 70% of the breath for exhaling. By selecting doses of the therapeutic gas for 30% of the breath time, a possible savings of 70% of the therapeutic gas can be achieved over the normal hospital system of having a constant flow. It is also possible to apply the therapeutic gas at a very early stage of inspiration with a large volume of gas which will reach the alveoli and not waste additional gas that remains in the "dead spaces" such as the pharynx, trachea, and bronchial tubes.

At the time the therapeutic gas flows into the inhalation sensor 28, high pressure is applied to the diaphragm 21, causing it to be in close contact with the circular recessed surface of the central cavity 23, moving the infrared-opaque vane 27 downward to block the infrared light of the interrupter module 25. Therefore, upon completion of the dose time, a signal is sent by the inhalation sensor 28, to an electrical circuit that actuates the solenoid valve 30 to its closed position and shuts off the flow of therapeutic gas to the inhalation sensor 28, and the cannula 1.

Upon completion of the user's exhaling, the cycle of events will be repeated by the user again inhaling.

Figure 9:
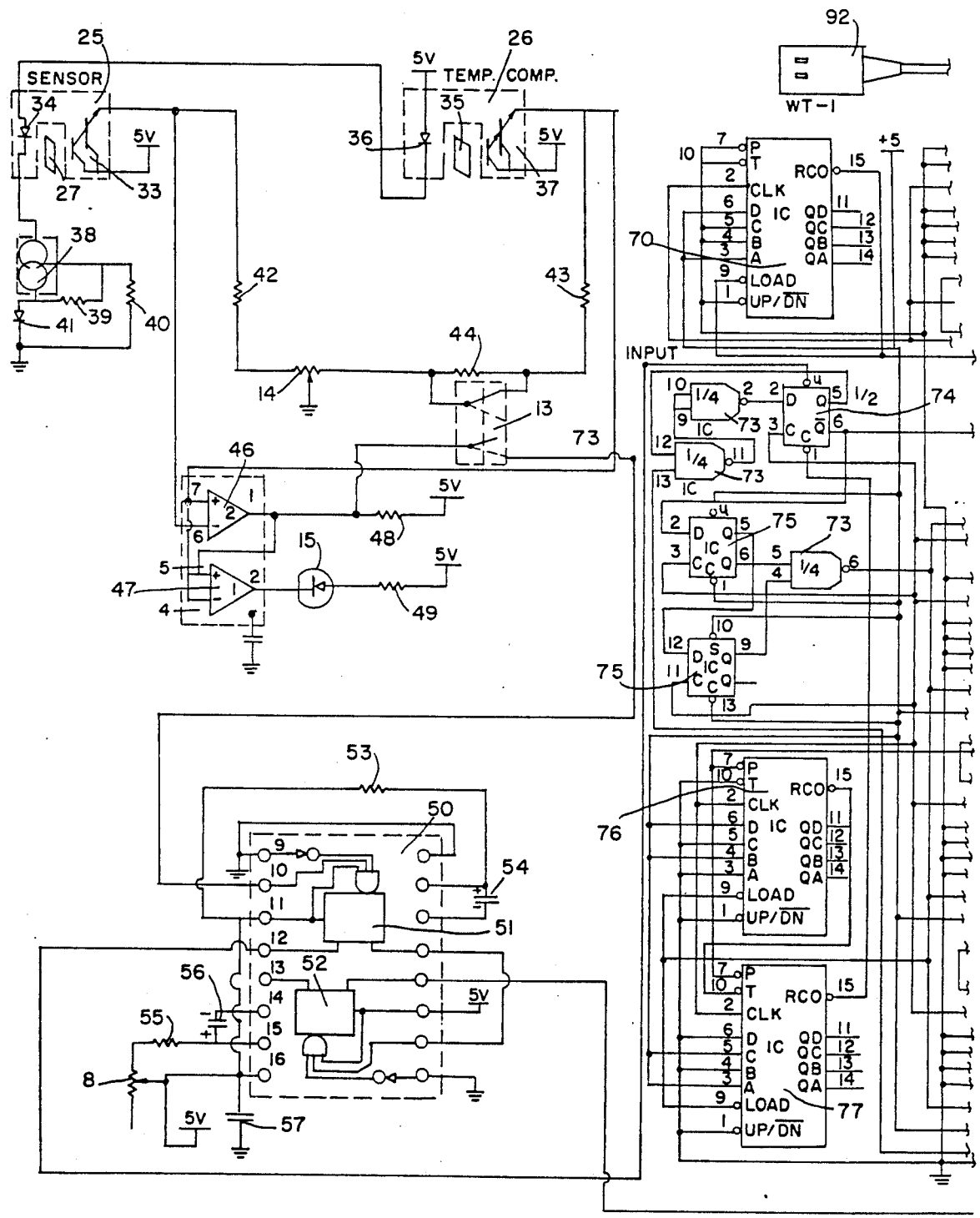
FIG. 9 is a schematic diagram of the respiratory therapy apparatus having automatic adjustment of the dose of therapeutic gas to the rate of breathing according to the invention.
Figure 9:
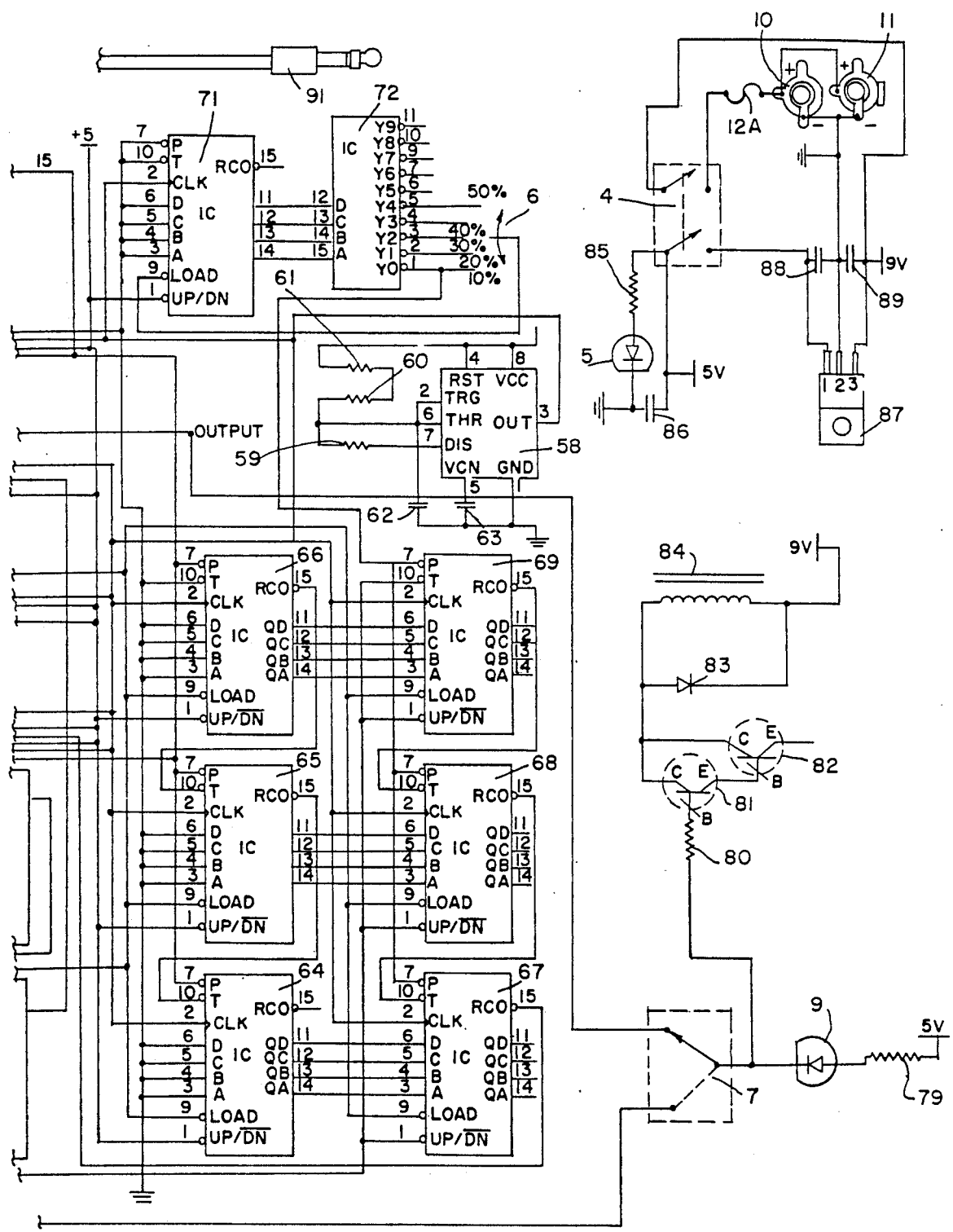

FIG. 9 generally illustrates a schematic diagram of one of the preferred means of electrical circuits used to obtain the two modes of operation to obtain intermittent flow of the therapeutic gas.

The movement of the diaphragm 21 will result in the infrared-opaque vane 27 interrupting the infrared light beam emitting from a gallium arsenide diode 34, FIG. 9, which is normally coupled to a silicon darlington connected phototransistor 33, which is housed in a solid state photon coupled interrupter module 25.

The second solid state photon coupled interrupter module 26 is used for temperature compensation to balance the temperature changes of the other module 25. Movement of vane 35 by manual adjustment will result in interrupting the infrared light beam emitting from the gallium arsenide diode 36 of FIG. 9 which is normally coupled to a silicon darlington connected phototransistor 37, FIG. 9, which is housed in the solid state photon coupled interrupter module 26.

The interrupter module 26 is mechanically adjusted for an electrical output equal to that of the electrical output of the other module 25 by adjusting vane 35.

The outputs of diodes 34 and 36 are made to have consistent infrared emitted light output over a wide temperature range by connecting the diodes in series and supplying them with a constant fixed current by use of a three terminal adjustable current source 38 that has a zero temperature coeffecient established by using resistors 39 and 40 with diode 41.

The outputs of the module 25 and the module 26 are connected to resistors 42 and 43 respectively which are connected to an adjusting potentiometer 14 which has it's movable tap connected to ground. The potentiometer 14 is adjusted to obtain maximum sensitivity of the optoelectronic sensor 28.

Resistor 44 prevents possible oscilations by slightly desensitizing the maximum sensitivity obtained when calibrating the apparatus by inserting resistor 44 when switch 13 is pressed into the operate position.

The electrical output of the module 25 is fed into the inverting input of voltage comparator 46. The electrical output of the module 26 is fed into the non-inverting input of a voltage comparator 46.

The voltage output of the comparator 46 is fed into a non-inverting input of comparator 47. A reference voltage is obtained from the output of a silicon darlington connected phototransistor 37 which is fed into the inverting input of the comparator 47.

The output voltage of comparators 46 and 47 will swing from full "ON" to full "OFF" when the voltage applied to the inputs differs by about 0.001 volts. Thus a very small movement of vane 27 will produce a very small voltage change that will result in the output of the comparators 46 and 47 swinging from full "OFF" to full "ON" with the voltage being applied to output resistors 48 and 49.

The output of the comparator 46 is fed to integrated circuit 50 which is two fully independent monostable multivibrators 51 and 52. Monostable multivibrator 51 is triggered by the output of comparator 46 to provide a basic one short time interval that provides an output to the mode 1 circuits where the dosage of therapeutic gas is based on a percentage of the time between breaths, and an output to mode 2, which is used to trigger monostable multivibrator 52 to provide a dosage of therapeutic gas where the length of time of the dosage is set by the user by adjusting control 8.

Switch 7 is used to select one of the two modes of operation. Resistor 53 and capacitor 54 are used to obtain a pulse with a fixed short time period from the monostable multivibrator 51.

Potentiometer control 8 in series with resistor 55 and capacitor 56 is used to obtain the variable time period for mode 2 operation using the monostable multivibrator 52. Capacitor 57 is used to remove power supply spikes. The LED (light emitting diode) 15 is used for calibrating to indicate when proper maximum sensitivity is obtained.

The output of the monostable multivibrator is used to actuate the "percentage" mode 1 of the apparatus that uses circuits that consist mainly of clock and counters. The basic concept is the enabling of two counters at two different rates. The two counters consist of one counter that counts up and another that counts down. When the sensor detects inhalation, it resets the "up" counter to zero and allows it to start counting. When the apparatus detects the next inhalation, it loads the value reached by the "up" counter into the "down" counter, resets the "up" counter to zero, and allows the "down" counter to count down to zero. The apparatus will administer therapeutic gas beginning when the "down" counter is loaded and ending when it reaches zero.

Different percentages of the length of breath makes it possible to administer the therapeutic gas at different percentages of the breath because both the "up" and "down" counters are run on different clocking schemes. They both actually run on the same clock, but are "enabled" to run at different percentages of the master clock frequency.

The master clock consists of the integrated circuit 58, resistors 59, 60, 61, and capacitors 62 and 63 which outputs a squarewave at approximately 450 Hz. All chips used for the mode 1 operation are clocked on this signal.

The two counters each consist of three cascaded up/down counter integrated circuits (up counter IC64, IC65, and IC66; down counter IC 67, IC68, and IC69). The three cascaded integrated circuits give a counting range of 12 bits, to enable a count up to $2^{12} = 4096$.

Next IC70 is a counter integrated circuit used to count down from nine to zero again and again in a loop. The "carry" output is directed into the "load" input, so that every time the counter reaches zero it outputs a carry pulse which loads nine into the counter, thus beginning the cycle over again. This "carry" pulse is used to enable the "up" counter (IC64, IC65, and IC66). In this configuration it enables the "up" counter every ten clicks of the master clock. Thus the "up" counter is running at one tenth of the master clock frequency.

The combination of the integrated circuits IC71 and IC72 form another counting loop. Integrated circuit IC71 is a counter wired to count up. Integrated circuit IC72 is a decoder that takes a binary input and outputs a pulse at the corresponding "decimal numbered" pin. Two integrated circuits IC71 and IC72 are used to create a variable timing loop. By sending the binary output of integrated circuit IC71 into the input of the decoder, and sending the desired "decimal numbered" pulse into the "load" input of the counter, the integrated circuits operate in a loop. For example, direct the decoder's output for "three" into the load input of the counter, and load zero into the counter, this results in a loop which outputs a pulse every fourth count (1, 2, 3, 0 pulse..). The rotary switch 6 is used to select the number of counts in this loop. The output pulse of this configuration is then sent to enable the "down" counter IC67, IC68, and IC69. The down counter runs at a variable percentage of the master clock frequency.

The above clocking/counting scheme is used to allow the apparatus to know a specific percentage of a given time between inhalations; for example, setting the unit at 40%. The "up" counter is allowed to count up to 500 in the time between inhalations, the master clock counts to 5000 clicks in the same time (the "up" counter is running at one-tenth of the master clock frequency). The number 500 is loaded into the "down" counter, which commences counting down. Since the apparatus is set at 40%, the "down" counter is enabled once every four clicks of the master clock, so it takes $4 \times 500 = 2000$ clicks of the master clock for the "down" counter to count down to zero, and 2000 is 40% of 5000.

Integrated circuits consisting of IC73, IC74, and IC75 are used as an interface to the output of the monostable multivibrator 51, and as the input to switch 7. The presence of an input pulse (from pin 12 of monostable multivibrator 51) serves to set one of the flip-flops on integrated circuit IC74. This turns on the flow of respiratory gas. The combination of the two flip-flops on integrated circuit IC75 and a NAND gate on integrated circuit IC73 serve to send a pulse (which is exactly one master-clock pulse long) to load the "down" counter and to reset the "up" counter. When the "down" counter reaches zero its "carry" output sends a pulse through two NAND gates on integrated circuit IC73 to the flip-flop on integrated circuit IC74. This pules toggles the flip-flop's output and stops the flow of respiratory gas.

The portion of the circuit which limits the apparatus to a dosage of respiratory gas for approximately two seconds, consists of IC76 and IC77 which are counters in a "down" counter configuration. These "down" counters are run on the main clock, and enabled at the same rate as the "up" counter, that is 45 Hz. When a breath is taken the number "90" is loaded into this counter, and it commences counting down. When it reaches "0", the "carry" output sends a pulse to the reset input of the flip-flop on IC74. This pulse resets the output and stops the flow of respiratory gas. The flow of respiratory gas dosage is limited as follows: the counter running at 45 Hz takes $1/45 = 0.0222$ seconds for one count. The counter loaded with a value of "90" counts down to "0" so that $90 \times 0.0222 = 2$ seconds.

The apparatus is able to give a dose of respiratory gas as a percentage of the time between inhalations, with a maximum dosage limit of two seconds.

The maximum amount of time between breaths for which the respiratory apparatus will be effective, is the highest number to which the "up" counter can count, which is 4096. If the master clock is running at 450 Hz, and the "up" counter is running at one tenth of this time, the "up" counter must be running at 45 Hz. It, therefore, takes 1/45=0.022 seconds for the "up" counter to count one click. When this counter counts to 4096 the maximum time allowable between breaths is 4096×0.022 seconds, which equals approximately 91 seconds.

Switch 7 determines which mode of operation is desired. The first mode of operation obtains a signal from the clock circuitry and provides a dosage of therapeutic gas that is determined by using a percentage of the time between breaths. The second mode of operation obtains a signal from the monostable multivibrator 52 and provides a dosage of therapeutic gas where the length of time of the dosage is set by the user adjusting control 8 to the desired time, such as 0.5 to 2.0 seconds.

The common connection of switch 7 provides for the signal that determines the length of dose to be applied to the LED (light emitting diode) 9 with its current limiting resistor 79 to indicate when a dose of the respiratory gas is being delivered, and a parallel connection to the load resistor 80 that results in the solenoid valve 30 being open when the dose is administered.

Resistor 80 load is applied to the transistors 81 and 82 which results in the coil 84 of the solenoid valve 30 being de-energized when a dose is administered. The diode 83 prevents voltage peaks from coil 84 affecting the transistors 81 and 82.

Jacks 10 or 11 provide the necessary 6-24 volts direct current necessary to provide power to the respiratory apparatus. The DC voltage can be obtained from plug 91 that is connected to the wall transformer 92 that converts 120 volts AC to 9 volts DC. The DC voltage can also be obtained from other sources, such as a car battery.

The DC voltage obtained above is applied to the voltage regulator 87 that regulates and provides a steady 5 volts DC to operate the respiratory apparatus. Capacitors 88 and 89 are by-pass capacitors connected to ground. Fuse 12A prevents accidental overloads from damaging the apparatus. Switch 4 is the power switch for turning the apparatus on and off. The LED (light emitting diode) 5 with its current limiting resistor 85, indicates when power is off or on.

I have now described my invention in considerable detail. However, it is obvious that others skilled in the art can build and devise alternate and equivalent constructions and circuit arrangements which are within the spirit and scope of the invention. Hence I desire that my protection be limited, not by the construction described, but only by the proper scope of the claims.

I claim:

1. In a respiratory therapy apparatus using intermittent flow having automatic adjustment of a dose of respiratory gas to a rate of breathing of an air-breathing animal, including human user, comprising:

means for delivering doses of respiratory gas to a user including means connecting the air breathing animal, including human user, to the respiratory therapy apparatus for sensing inhalation, means connecting the respiratory apparatus to a source of adjusted regulated flow of respiratory gas, means for sensing inhalation, means for generating an electrical signal upon sensing inhalation and means for generating another electrical signal upon sensing a next consecutive inhalation, means for measuring the length of time between said electrical signals, whereby said measured length of time constitutes the length of a previous breath, said means for delivering doses of respiratory gas to a user includes means for selecting a percentage of the measured length of time of a previous breath; said percentage determining the duration of a dose of respiratory gas which is delivered to a user during a next consecutive inhalation;

said means for delivering doses of respiratory gas to a user further includes means for limiting the duration of a dose to a time which is less than the length of a previous breath.

2. An apparatus for respiratory therapy as recited in claim 1, further comprising:

means for temperature compensation.

3. An apparatus for respiratory therapy as recited in claim 1, further comprising:

means for calibration.

4. In a respiratory therapy method using intermittent flow having automatic adjustment of a dose of respiratory gas to a rate of breathing of an air-breathing animal, including human user, comprising:

providing means for delivering doses of respiratory gas to a user including means connecting the air breathing animal, including human user, to the respiratory therapy apparatus for sensing inhalation, providing means connecting the respiratory apparatus to a source of adjusted regulated flow of respiratory gas, providing means for sensing inhalation, generating an electrical signal upon sensing inhalation and generating another electrical signal upon sensing a next consecutive inhalation, measuring the length of time between said electrical signals, whereby said measured length of time constitutes the length of a previous breath, delivering doses of respiratory gas to a user and selecting a percentage of the measured length of time of a previous breath; said percentage determining the duration of a dose of respiratory gas which is delivered to a user during a next consecutive inhalation;

said step of delivering doses of respiratory gas to a user further includes limiting the duration of a dose to a time which is less than the length of a previous breath.

* * * * *